United States Patent
Krebs et al.

(10) Patent No.: US 9,144,496 B2
(45) Date of Patent: Sep. 29, 2015

(54) INSERTER CONNECTION MEMBER

(71) Applicant: Zimmer, Inc., Warsaw, IN (US)

(72) Inventors: Robert D. Krebs, Warsaw, IN (US); Sarah E. Helt, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 85 days.

(21) Appl. No.: 13/867,412

(22) Filed: Apr. 22, 2013

(65) Prior Publication Data

US 2013/0282133 A1 Oct. 24, 2013

Related U.S. Application Data

(60) Provisional application No. 61/637,095, filed on Apr. 23, 2012.

(51) Int. Cl.
*A61F 2/32* (2006.01)
*A61F 2/34* (2006.01)
*A61F 2/46* (2006.01)
*A61F 2/30* (2006.01)

(52) U.S. Cl.
CPC ... *A61F 2/34* (2013.01); *A61F 2/46* (2013.01); *A61F 2/4609* (2013.01); *A61F 2/3094* (2013.01); *A61F 2002/302* (2013.01); *A61F 2002/3054* (2013.01); *A61F 2002/30484* (2013.01); *A61F 2002/30505* (2013.01); *A61F 2002/4628* (2013.01)

(58) Field of Classification Search
CPC ...... A61F 2/34; A61F 2/36; A61F 2002/3625
USPC ............................................. 623/22.1–22.39
See application file for complete search history.

(56) References Cited

U.S. PATENT DOCUMENTS

| | | | |
|---|---|---|---|
| 5,904,688 A | 5/1999 | Gilbert et al. | |
| 6,087,553 A | 7/2000 | Cohen et al. | |
| 6,589,284 B1* | 7/2003 | Silberer | 623/22.29 |
| 7,341,593 B2 | 3/2008 | Auxepaules et al. | |
| 2004/0186586 A1* | 9/2004 | Seyer et al. | 623/22.12 |
| 2007/0219562 A1* | 9/2007 | Slone et al. | 606/99 |

* cited by examiner

*Primary Examiner* — Jason-Dennis Stewart
(74) *Attorney, Agent, or Firm* — Schwegman Lundberg & Woessner, P.A.

(57) ABSTRACT

An apparatus can include an acetabular cup, and a connection member that can be mounted to the acetabular cup such as near a rim edge of the acetabular cup. The connection member can include an attachment section that can be configured to receive an attachment from an inserter. The attachment section can be configured to permit the inserter to be attached to the connection member in two or more different orientations relative to the connection member.

10 Claims, 10 Drawing Sheets

INSERTER CONNECTION MEMBER

CLAIM OF PRIORITY

This application claims the benefit of U.S. Provisional Patent Application Ser. No. 61/637,095 filed on Apr. 23, 2012, the benefit of priority of which is claimed hereby, and which is incorporated by reference herein in its entirety.

FIELD

The present subject matter relates to an orthopedic system and specifically to an inserter connection member for a prosthetic acetabular cup.

BACKGROUND

In a hip replacement procedure, an orthopedic implant assembly in the form of an acetabular cup can be implanted within an acetabulum of a patient. A cup inserter is attached to the acetabular cup and used to insert and position the cup within the acetabulum. A femoral component can be mated to the acetabular cup to complete the hip replacement procedure.

For proper performance of the device, the acetabular cup should be properly positioned in the acetabulum. U.S. Pat. Nos. 5,904,688 and 7,341,593 discuss acetabular cups and related insertion tools.

OVERVIEW

An acetabular cup can include a connection member that can be mounted to the acetabular cup near a rim edge of the acetabular cup. The connection member can include an attachment section that can be configured to receive an attachment from an inserter. The attachment section can be configured to permit the inserter to be attached to the connection member in two or more different orientations relative to the connection member.

The connection member can include a ring. The attachment section can include a plurality of separate attachment projections that can be located around an external upper edge of the ring. The attachment projections can include connection surfaces extending from the connection member body. The plurality of attachment projections can be positioned equidistant from each other. The attachment section can include an unbroken groove, such as extending around an outer perimeter of the ring. The connection member can include a plurality of holes, such as can be located around a body of the connection member. The connection member can be positioned between an outer shell of the acetabular cup and an inner bearing member of the acetabular cup. The attachment section can be located above an edge rim surface of the outer shell.

In an example, an acetabular cup can include an outer shell and an inner bearing surface. An annular connection member can be configured to mount to the acetabular cup near a rim edge of the acetabular cup between the outer shell and the inner bearing surface. The annular connection member can include an attachment section that can be located around the annular connection member's upper perimeter. The attachment section can be configured to receive an attachment from an inserter. The attachment section can be configured to permit the inserter to be removably attached to the annular connection member, such as in two or more orientations relative to the connection member.

The acetabular cup can include a mono-block acetabular cup, such as described and claimed in U.S. Pat. No. 6,087,553, which is hereby incorporated by reference in its entirety. The attachment section can include a plurality of separate attachment projections, such as can be located around an external upper edge of the annular connection member. The attachment section can include a groove, such as extending around an outer perimeter of the annular connection member. The groove can include an unbroken groove, such as extending around the entire outer perimeter of the annular connection member. The attachment section can be located above an edge rim surface of the outer shell.

A method of use can include attaching an inserter to an acetabular cup in a first orientation chosen from multiple possible orientations. The acetabular cup can be inserted into an acetabulum using the inserter. The inserter can be removed from the acetabular cup.

The method can further include removing the acetabular cup from the inserter and re-attaching the inserter to the acetabular cup in a second orientation, different from the first orientation. The inserted acetabular cup can include a mono-block acetabular cup. The inserted acetabular cup can include an outer shell and an inner bearing surface, and an annular connection member that can be configured to mount to the acetabular cup near a rim edge of the acetabular cup. The annular connection member can include an attachment section, such as can be located around the annular connection member's upper perimeter. The attachment section can be configured to receive an attachment from an inserter. The attachment section can be configured to permit the inserter to be removably attached to the annular connection member, such as in two or more orientations relative to the connection member. The attachment section can include an unbroken groove, such as extending around the entire outer perimeter of the annular connection member.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
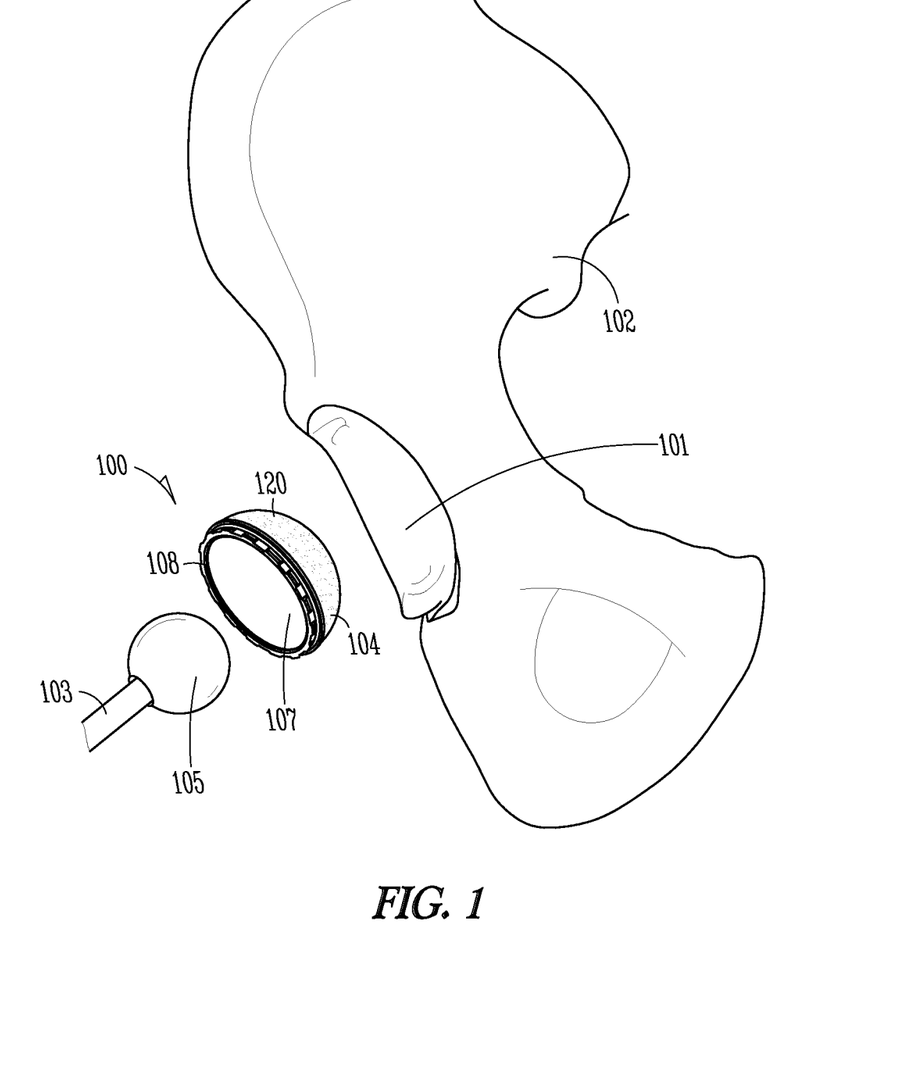
FIG. 1 shows a perspective view of an acetabular cup and femoral component.

FIG. 1 shows a perspective view of an example of an acetabular cup 100 and a femoral component 103. In this prosthetic system, the acetabular cup 100 can be configured to be mounted to an acetabulum 101 of a patient's hip bone 102. The femoral component 103 can be attached to the patient's femur. The femoral component 103 can include a femoral head 105 that can be configured to mate with the acetabular cup 100 when the acetabular cup 100 receives the femoral head 105 of the femoral component 103.

In this example, acetabular cup 100 can be a monoblock-type acetabular cup and can include an outer shell 104, an inserter connection member 108, and an inner bearing surface 107. The outer shell 104 can include a hemispheric or other semispheric shape. An outer surface 120 can be adapted to attach to the acetabulum 101. The inner bearing surface 107 can include or be formed from a polymeric material, such as ultra-high-molecular weight polyethylene. The outer shell 104 can be porous. The outer shell 104 can include or be formed of a metallic outer shell 104. The metallic outer shell 104 can include or be formed of a fiber metal shell that can surround the polymeric material and can provide a surface that can permit bony ingrowth or anchoring of bone cement. For example, the outer surface 120 can include or be formed of a material adapted to promote bone growth to the outer surface 120. The outer shell 104 can include or be formed from a porous metallic material for the outer shell 104. One example includes a porous tantalum structure, for instance a porous tantalum structure such as TRABECULAR METAL®, available from Zimmer Inc., Warsaw, Ind. The porous tantalum structure can be configured to facilitate osseointegration. The porous tantalum structure can have a pore size, pore continuity, and other features for facilitating bone tissue growth into the pores. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is incorporated herein by reference. An inner bearing surface 107 can include or be formed of a ceramic material. The acetabular cup 100 can be formed as an all polymeric cup, an all metal cup, or any other suitable material or combination thereof suitable for a particular application.

Figure 2:
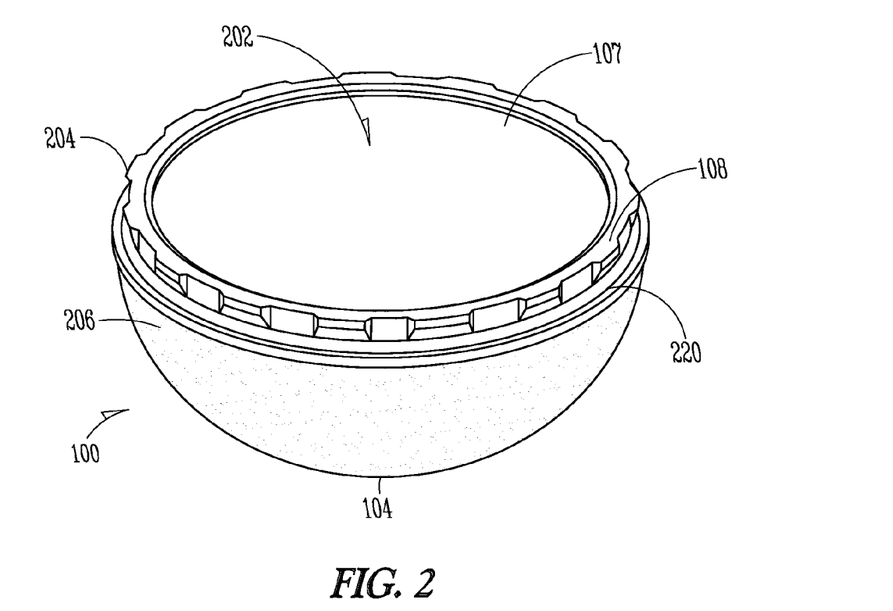
FIG. 2 shows a perspective view of the acetabular cup of FIG. 1.

FIG. 2 shows a perspective view of the acetabular cup 100. The acetabular cup 100 can include a cavity 202, such as for receiving a femoral head. An annular face 204 can bound the cavity 202 and can define a rim edge 206. The inserter connection member 108 can be mounted to the acetabular cup 100, such as near the rim edge 206 of the acetabular cup such that it is at least partially exposed for grasping by an inserter.

Figure 3:
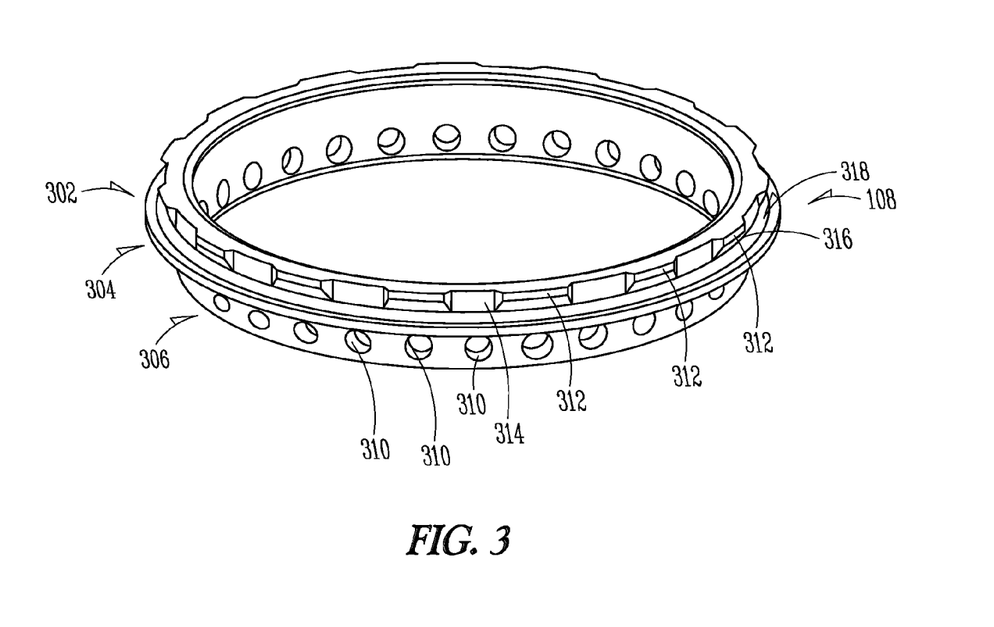
FIG. 3 shows a perspective view of an inserter connection member for the acetabular cup of FIG. 1.

FIG. 3 shows a perspective view of the inserter connection member 108 for the acetabular cup 100. The inserter connection member 108 can be formed of metal, ceramic, or one or more other suitable materials. The inserter connection member 108 can include an annular ring shape that can include an upper inserter attachment section 302 that can be configured to receive an attachment, such as from an inserter. The attachment section 302 can be configured to permit the inserter to be attached to the connection member 108 in two or more orientations relative to the connection member 108. The inserter attachment section 302 can include a plurality of equidistantly spaced attachment projections 312, such as can be separated by respective notches 314. The attachment projections 312 can be located around the entire upper perimeter portion of the connection member 108. An individual attachment projection 312 can include an upwardly sloping connection surface 316 that can extend outward from the body of the connection member 108. An attachment area 318 can be located beneath the sloping connection surface 316. An inserter can attach to the connection member 108, such as with fingers extending into the attachment area 318 and then tightening or clamping together to hold tight against connection surface 316. The attachment section 302 can be configured to receive an attachment from an inserter in two or more orientations relative to the connection member 108. The plurality of evenly spaced attachment projections 312 can allow for multiple points of contact around the upper periphery of an acetabular cup.

The inserter attachment member 108 can include a central ridge 304 and a lower portion 306. The lower portion 306 can include a plurality of holes 310 extending through the lower portion 306.

In FIG. 2, the acetabular cup 100 can be assembled by press-fitting the inserter connection member 108 at an upper rim edge 220 of the outer shell 104. The inserter connection member 108 can be positioned relative to the outer shell 104 such that the lower portion 306 confronts an inner surface of the outer shell 104 at the upper rim edge 220. The central ridge 304 can be located to contact the upper rim edge 220 surface. The attachment section 302 can be positioned and exposed above the upper rim edge 220. After the inserter connection member 108 is inserted into the outer shell 104, the inner bearing surface 107 can be molded into the cavity of the outer shell 104. The inner bearing surface 107 can include or be formed of a polyethylene material, such as antioxidant stabilized high molecular weight polyethylene as described and claimed in U.S. Pat. No. 8,129,440. When the inner bearing surface 107 material is first placed with the outer shell 104, the material can flow through holes 310 of the inserter connection member 108. This can help bond the inserter connection member 108 to the outer shell 104. Thus, the polyethylene material can be configured to form the inner bearing surface 107 and to flow through holes 310 of the connection member 108. This can help bond the connection member 108 to the outer shell 104 and to the polyethylene molded inner bearing surface 107, thus forming a unitary monoblock structure.

Because such a monoblock acetabular cup, as described above, need not require any attachment screws, it can be deeper set within the anatomy, but it can also be more difficult to grab, hold, and to properly orient the acetabular cup since the patient's anatomy may get in the way. The present inserter connection system can help by allowing for multiple orientations of the cup relative to the inserter, such as to allow the doctor to grab and tightly hold the acetabular cup 100 in any desired orientation.

Although described herein primarily for use with a mono-block acetabular cup, in some embodiments the inserter connection member 108 can be used with a modular multi-holed acetabular cup system. For example, the inserter connection member 108 can be mounted or fastened to an acetabular cup outer shell using one or any combination of one or more adhesives or one or more screws or one or more other fasteners. After the outer shell has been mounted to the acetabulum, an inner bearing surface, such as a ceramic bearing surface can then be positioned into the cavity of the outer shell.

Figure 4:
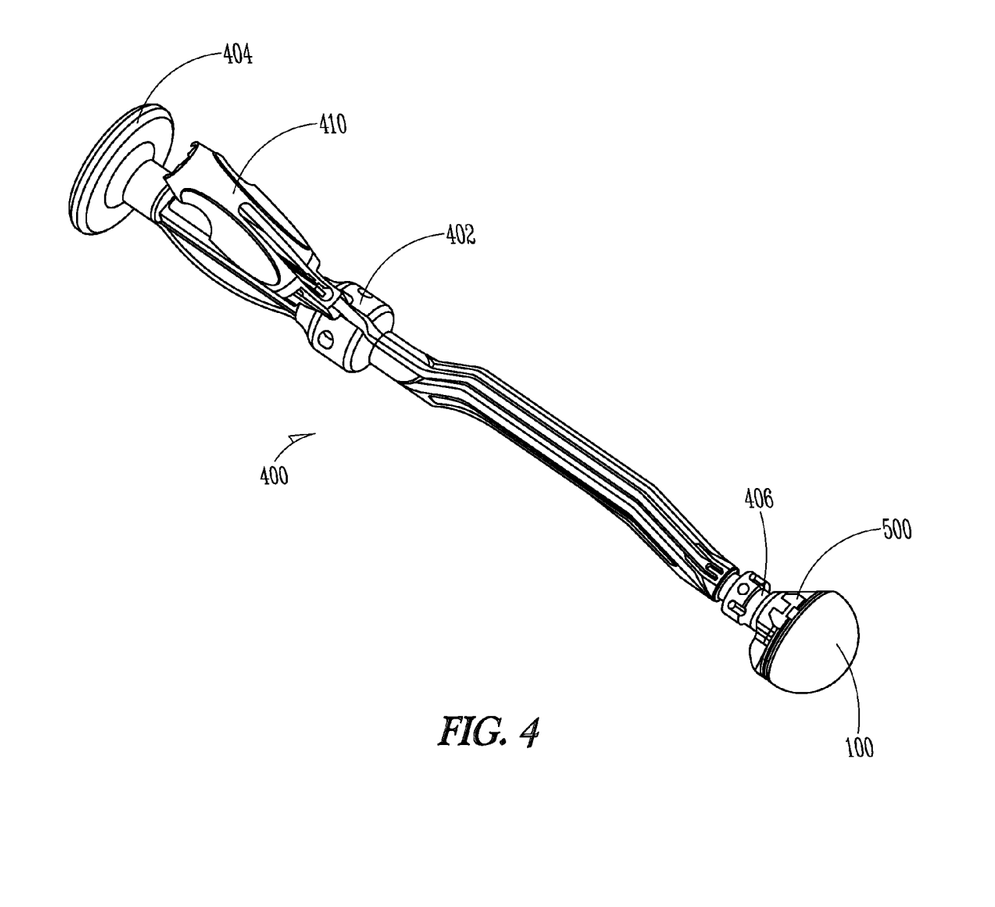
FIG. 4 shows a view of an inserter.
Figure 5:
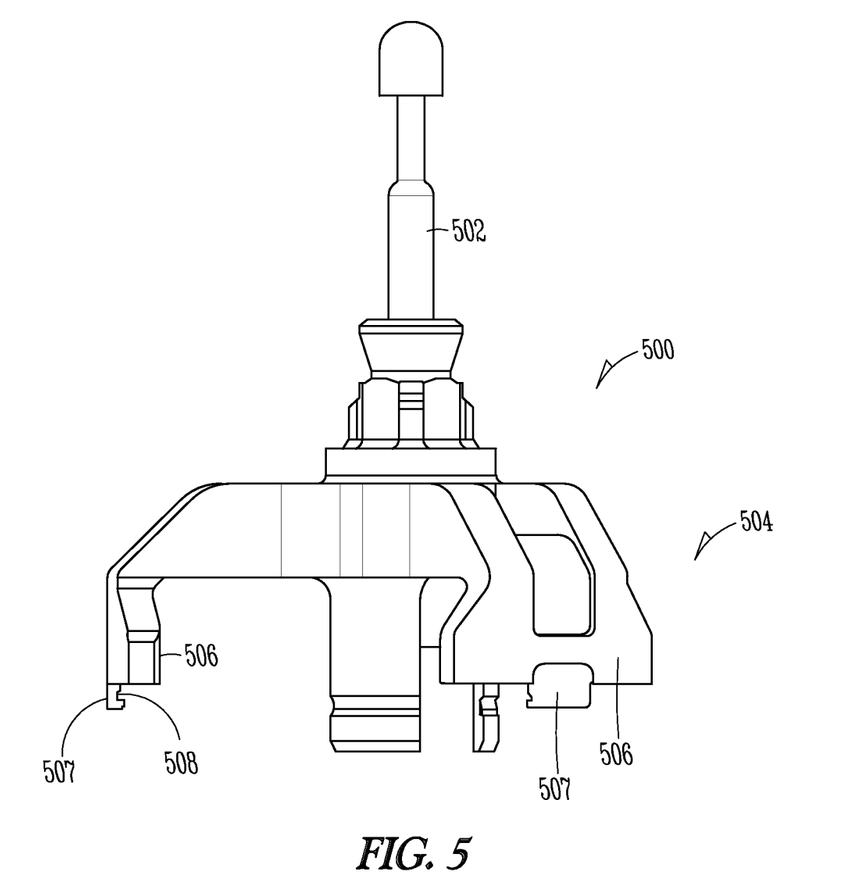
FIG. 5 shows an attachment for the inserter of FIG. 4.
Figure 6:
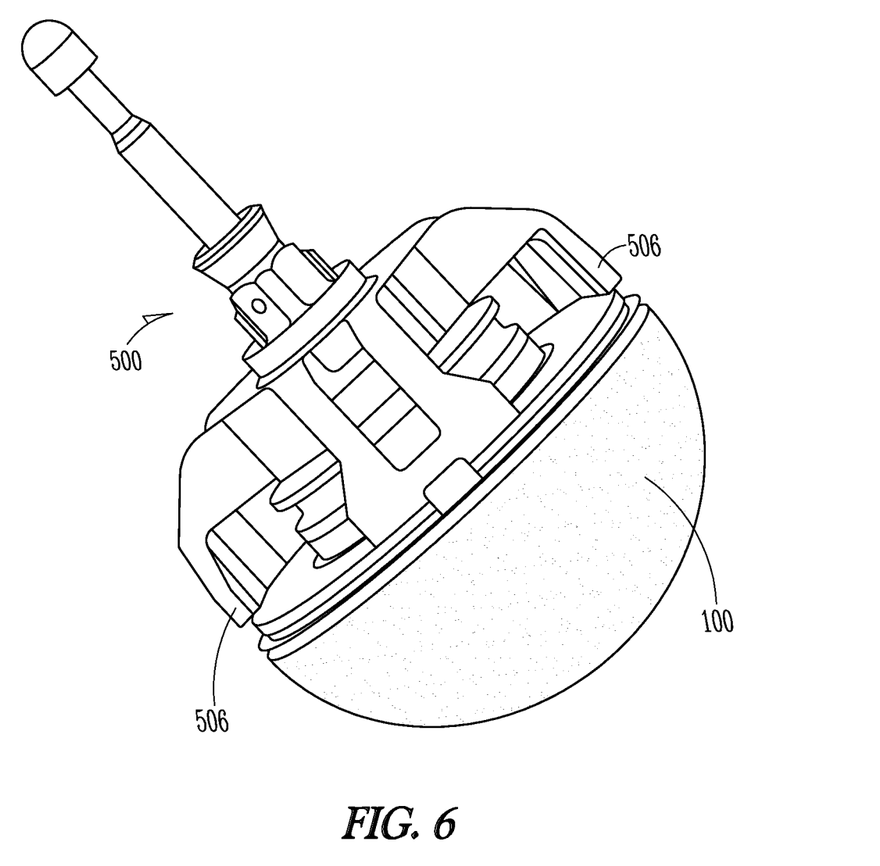
FIG. 6 shows a perspective view of the inserter attachment mounted to an acetabular cup in accordance with one or more embodiments.
Figure 7:
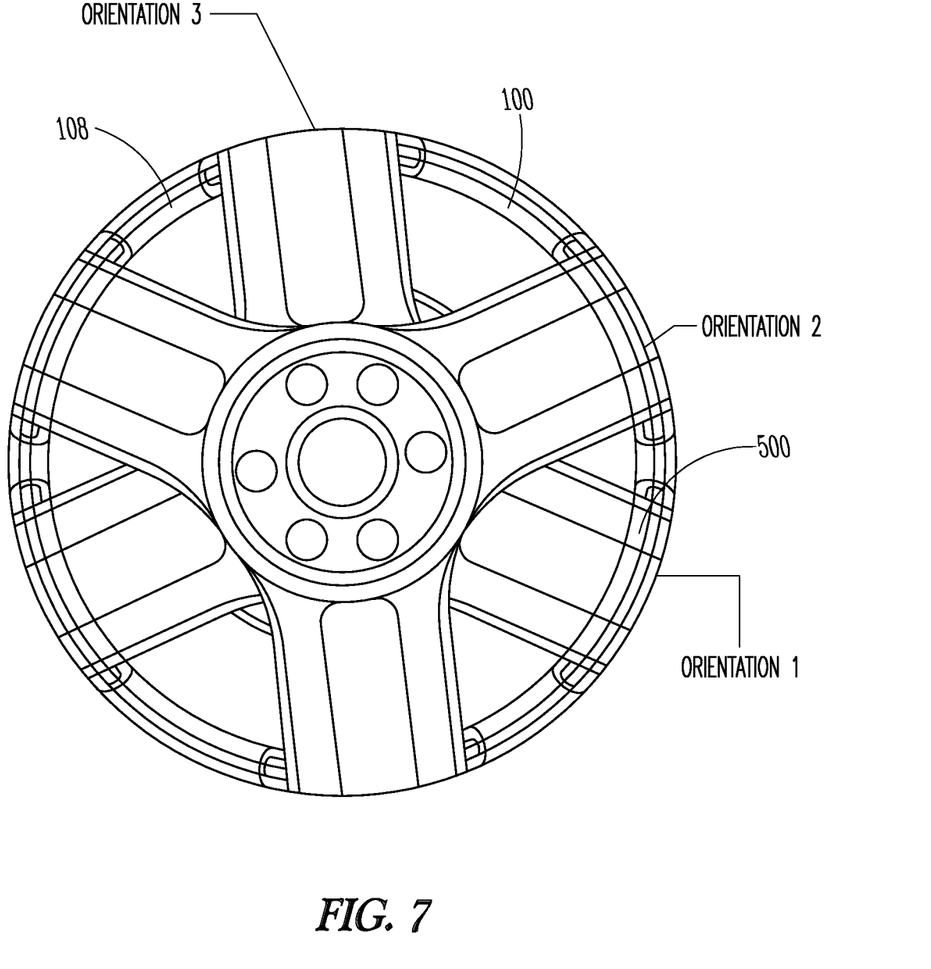
FIG. 7 shows a top view of the inserter attachment mounted to an acetabular cup.

FIGS. 4, 5, 6, and 7 show examples of details of an inserter 400, usable with the acetabular cup 100 described above. FIG. 4 shows a view of an example of the inserter 400; FIG. 5 shows an example of an inserter attachment 500 for the inserter 400 of FIG. 4; FIG. 6 shows a perspective view of an example of the inserter attachment 500 mounted to the acetabular cup 100; and FIG. 7 shows a top view of an example of the inserter attachment 500 mounted to the acetabular cup 100 in various orientations.

The inserter 400 can be used to orient the acetabular cup 100 in the acetabulum and to impact the acetabular cup 100. When an acetabular cup is inserted into the acetabulum, the doctor may find that different portions of the patient's anatomy gets in the way of different portions of the acetabular cup, which can make it difficult to get a proper grip on the acetabular cup with the inserter. The present inserter connection member 108 of the acetabular cup 100 can allow for multiple rotational orientations of the inserter relative to the upper perimeter of acetabular cup, such that the doctor can have many different positioning options.

The inserter 400 can include a handle 402 and the inserter attachment 500. The handle 402 can include a length and can have an impaction surface 404 at a proximal end and an attachment section 406 on the distal end of the handle 402, such as to permit attachment of the inserter attachment 500 to the handle 402. The handle 402 can include a locking lever 410 that can be configured to work with the inserter attachment 500, such as to clamp the insert attachment 500 to the inserter attachment member of the acetabular cup 100.

The inserter attachment 500 can include a mounting section 502 that can be sized or shaped or otherwise adapted to matingly attach to the corresponding attachment section 406 of the handle 402. The inserter attachment 500 can include an attachment section 504 that can be configured to be removably attached to the attachment section 302 of the inserter connection member 108 of the acetabular cup 100.

The inserter attachment 500 can be sized or shaped or otherwise adapted to firmly hold and allow impaction of an acetabular cup when the inserter attachment is attached to the mating handle 402. The attachment section 504 can include two or more arms 506 that can have movable fingers 507. An undercut portion 508 on the fingers 507 can securely hold the acetabular cup when the inserter attachment 500 is clamped to the connection member 108 of the acetabular cup. The fingers 507 can be configured to be capable of being moved outward to allow the acetabular cup 100 to fit within the attachment section 504. Actuating the locking lever 410 can then clamp the fingers 507 inward, such as to lock the fingers 507 to the inserter connection member 108 of the acetabular cup 100. In FIG. 3, the finger 507 and the undercut portion 508 can be forced against the attachment projections 312 of the inserter connection member 108, forming a connection as shown in FIG. 6. Such a tight, secure connection can provide a more secure attachment than other approaches, such as an approach in which an inserter uses a threaded insertion device, which can loosen when impacted.

FIG. 7 shows an example of how the inserter attachment 500 can be attached to the acetabular cup 100, such as in two or more rotational orientations around the rim of the acetabular cup 100. The inserter attachment 500 diameter can be inside the diameter of the acetabular cup 100. This can help solve problems of anatomy obstructing the acetabular cup during insertion into or removal from the patient.

In an example of use, the inserter attachment can be attached to the acetabular cup 100 at any given orientation chosen by the doctor. The inserter can then be used to push or position the acetabular cup within the patient's acetabulum. At any time, the doctor can change the orientation of the inserter relative to the cup, such as based on anatomy, cup placement issues, or ease of insertion. After reorientation of the inserter relative to the cup, the doctor can resume insertion. When the cup is properly positioned, the inserter can then be impacted, such as to drive the cup to its final position. The inserter can then be removed from the acetabular cup and the orthopedic procedure can continue.

Figure 8:
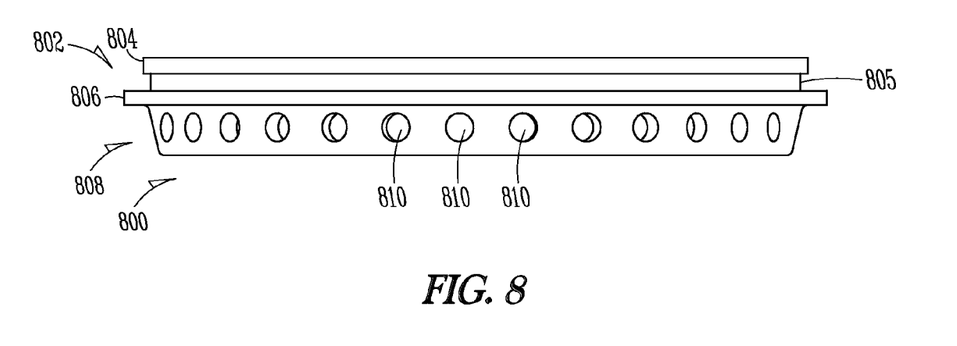
FIG. 8 shows a side view of a connection member.
Figure 9:
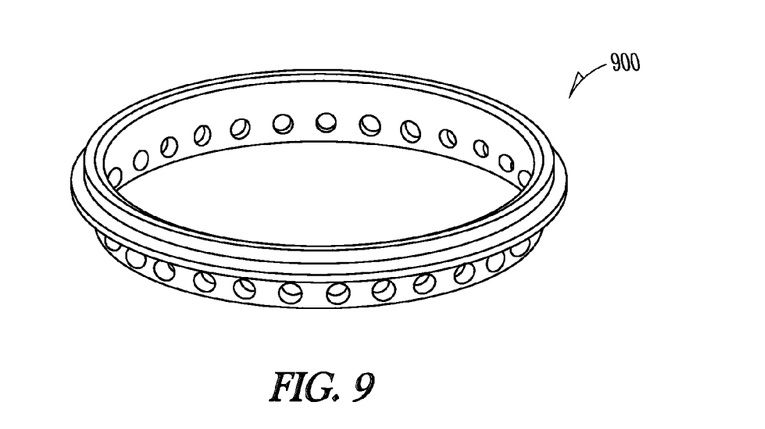
FIG. 9 shows a top perspective view of the connection member of FIG. 8.

FIG. 8 shows a side view of an example of an inserter connection member 800; and FIG. 9 shows a top perspective view of the connection member 800. The inserter connection member 800 can include some similar features as inserter connection member 108 discussed herein and that discussion is incorporated herein by reference.

The inserter connection member 800 can include an annular ring shape that can have an upper inserter attachment section 802, a central ridge 806 and a lower portion 808. The lower portion 808 can include a plurality of holes 810 extending through the lower portion 808.

The upper inserter attachment section 802 can be configured to receive an attachment from an inserter. The attachment section 802 can be configured to permit the inserter to be attached to the connection member 800, such as in any rotational orientation relative to the connection member 800. The inserter attachment section 802 can include an upper ridge 804 and a connection section 801, such as a groove 805 that can extend around the perimeter of the attachment section 802. The groove 805 can be defined between an upper ridge 804 and a central ridge 806. The groove 805 can include an unbroken groove, such as extending around the entire perimeter of the connection member 800. This structure can permit virtually any rotational orientation of the inserter relative to the connection member 800 since the inserter can be attached to the connection member at any rotational orientation desired.

An inserter, such as described herein, can attach to the connection member 800 with the fingers extending into the groove 805 and then tightening or clamping together, such as to hold tight against the connection member.

A mono-block acetabular cup 100 can be formed using the connection member 800 in the same manner as described herein for connection member 108. The inserter connection member 800 can be used with a modular multi-holed acetabular cup system, such as in a similar manner as described herein for connection member 108.

Figure 10:
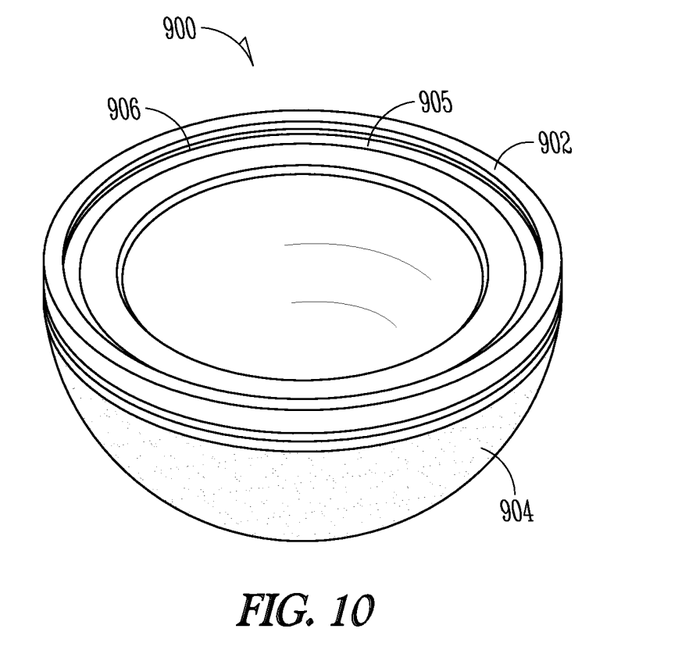
FIG. 10 shows a top perspective view of an acetabular cup in accordance with one or more embodiment.

FIG. 10 shows a perspective view of an acetabular cup 900, in accordance with one embodiment. Acetabular cup 900 can include similar features as the acetabular cups discussed above. In this example, acetabular cup 900 can include an outer shell 904, an inserter connection member 902, and an inner bearing surface.

The inserter connection member 902 can include an annular ring shape that can include an upper inserter attachment section 905 that can be configured to receive an attachment, such as from an inserter. The attachment section 905 can be configured to permit the inserter to be attached to the connection member 902 in two or more orientations relative to the connection member 902. The inserter attachment section 905 can include an internal attachment groove 906 that extends around the interior perimeter of the inserter connection member 902. The groove 906 can be defined between an upper ridge and a lower ridge. The groove 906 can include an unbroken groove, such as extending around the entire interior perimeter of the connection member 902. This structure can permit virtually any rotational orientation of the inserter relative to the connection member 902 since the inserter can be attached to the connection member at any rotational orientation desired.

Figure 11:
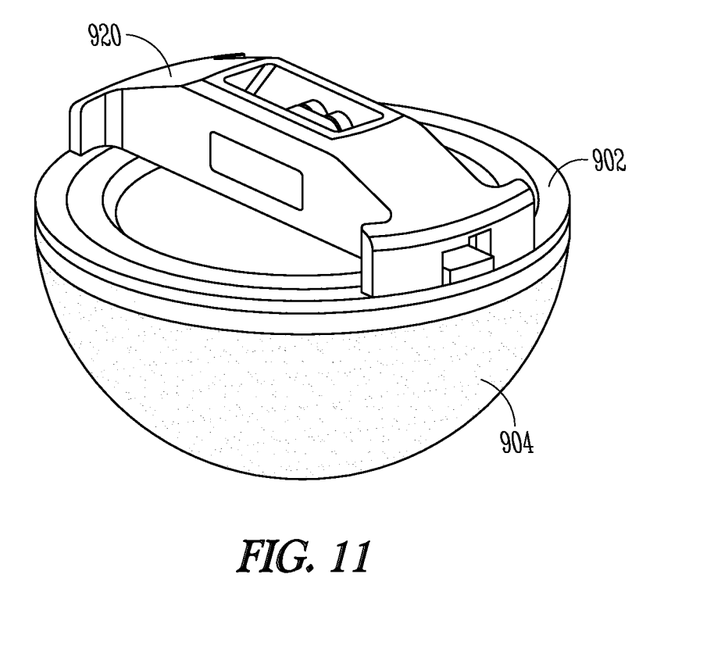
FIG. 11 shows a perspective view of an inserter attachment attached to the acetabular cup of FIG. 10.
Figure 12:
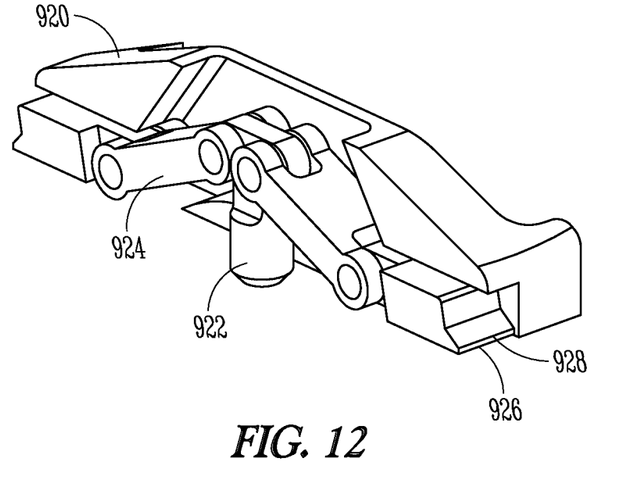
FIG. 12 shows a partial section view of the inserter attachment of FIG. 11 in accordance with one or more embodiments.

FIG. 11 shows a perspective view of an inserter attachment 920 attached to the inserter connection member 902. FIG. 12 shows a perspective view of the inserter attachment 920. The inserter attachment 920 can attach to the inserter connection member 902 with fingers 928 extending into the groove 906 and then tightening by spreading outward, to hold tight against the connection member 902.

Inserter attachment 920 can include an actuator 922, one or more links 924 rotatably coupled to the actuator 922, and opposing attachment grippers 926 rotatably attached to the links 924. The finger 928 at the distal end of the attachment gripper 926 is dimensioned to fit within the internal groove 906 of the inserter connection member 902.

In this example, the inserter attachment 920 has a relatively low profile and overall height since the inserter attachment 920 is designed to work with the internal groove 906 of the inserter connection member 902. Having an internal groove 906 allows the fingers 928 of the inserter attachment 920 to translate horizontally to attach to the inserter connection member 902. This horizontal movement allows for the lower profile.

When the inserter attachment 920 is attached to an inserter, such as inserter 400 discussed above, and then actuated, actuator 922 is pulled outward. This action causes the links 924 to rotate downward, which causes fingers 928 to be pushed horizontally outward.

Other examples can use other mechanisms for actuating the horizontal translation of the fingers of the inserter attachment.

Figure 13:
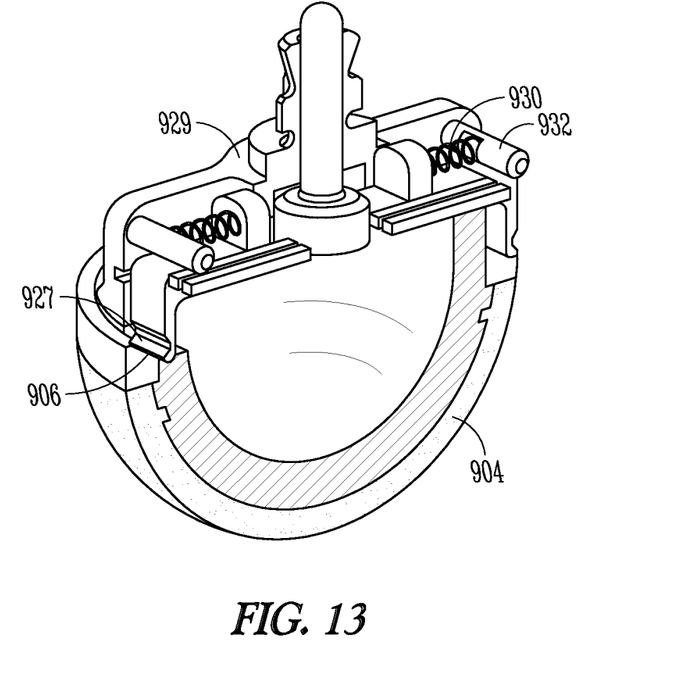
FIG. 13 shows a cross-section view of an inserter attachment attached to an acetabular cup in accordance with one or more embodiments.

FIG. 13 shows a cross-section view of an inserter attachment 929. In this example, inserter attachment 929 can include springs 930 that can apply force against abutments 932 to force fingers 927 into the groove 906.

Figure 14:
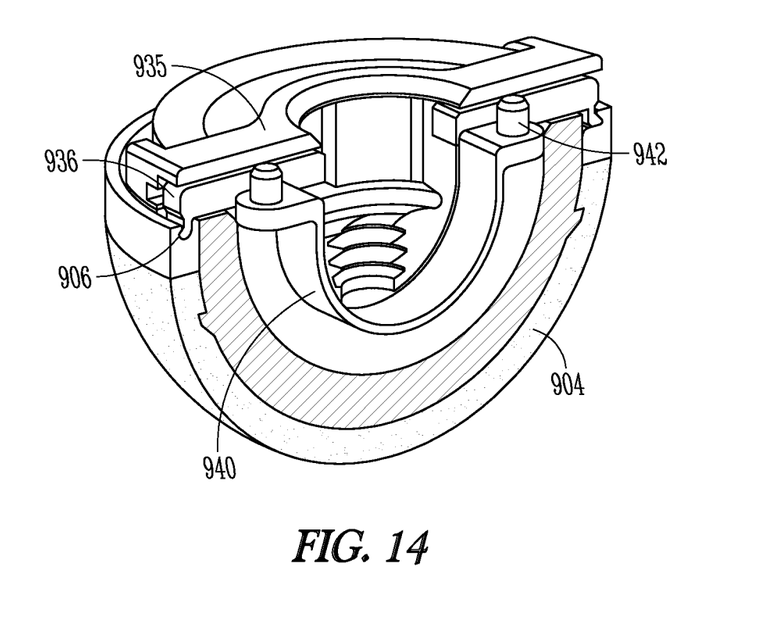
FIG. 14 shows a cross-section view of an inserter attachment attached to an acetabular cup in accordance with one or more embodiments.

FIG. 14 shows a cross-section view of an inserter attachment 935. In this example, inserter attachment 935 can include a U-shaped spring 940 which applies force against fingers 936 forcing the fingers 936 into the groove 906.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus comprising:
   an acetabular cup; and
   a connection member mounted to the acetabular cup near a rim edge of the acetabular cup;
   wherein the connection member includes an attachment section configured to receive an attachment from an inserter, wherein the attachment section includes an unbroken groove around an inner perimeter of the rim edge and is configured to permit the inserter to be attached to the connection member in any rotational orientation relative to the connection member.

2. The apparatus of claim 1, wherein the connection member includes a ring.

3. The apparatus of claim 1, wherein the connection member includes a plurality of holes located around a body of the connection member.

4. The apparatus of claim 1, wherein the connection member is positioned at least partially between an outer shell of the acetabular cup and an inner bearing member of the acetabular cup.

5. The apparatus of claim 4, wherein the attachment section is located above an edge rim surface of the outer shell.

6. An apparatus comprising:
   an acetabular cup including an outer shell and an inner bearing surface;
   an annular connection member configured to mount to the acetabular cup near a rim edge of the acetabular cup between the outer shell and the inner bearing surface;
   wherein the annular connection member includes an attachment section includes an unbroken groove around an inner perimeter of the rim edge and, the attachment section configured to receive an attachment from an inserter, wherein the attachment section is configured to permit the inserter to be removably attached to the annular connection member in any rotational orientation relative to the connection member.

7. The apparatus of claim 6, wherein the acetabular cup includes a mono-block acetabular cup.

8. The apparatus of claim 6, wherein the attachment section includes a groove extending around an outer perimeter of the annular connection member.

9. The apparatus of claim 8, wherein the groove includes an unbroken groove extending around the entire outer perimeter of the annular connection member.

10. The apparatus of claim 6, wherein the attachment section is located above an edge rim surface of the outer shell.

* * * * *